United States Patent
O'Brien et al.

(10) Patent No.: US 6,310,218 B1
(45) Date of Patent: Oct. 30, 2001

(54) MELT CRYSTALLIZATION PURIFICATION OF LACTIDES

(75) Inventors: William George O'Brien, Newark; Gilbert Jacob Sloan, Wilmington, both of DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 08/231,964

(22) Filed: Apr. 22, 1994

Related U.S. Application Data

(63) Continuation of application No. 08/028,773, filed on Feb. 17, 1993, now abandoned.

(51) Int. Cl.[7] ................................................. C07D 493/00
(52) U.S. Cl. ............................................................ 549/231
(58) Field of Search ............................................. 549/231

(56) References Cited

U.S. PATENT DOCUMENTS

| | | |
|---|---|---|
| Re. 32,241 | 9/1986 | Saxer . |
| 1,095,205 | 5/1914 | Gruter et al. . |
| 2,668,162 | 2/1954 | Lowe . |
| 4,797,468 | 1/1989 | Devries . |
| 4,835,293 | 5/1989 | Bhatia . |
| 5,053,522 | 10/1991 | Muller . |
| 5,264,592 | 11/1993 | Fridman et al. . |

OTHER PUBLICATIONS

Pavia et al., Intro. to Organic Laboratory Techniques, *Saunders Golden Sunburst Series*, pp. 505–516, 1976.
Wynn, Separate Organics by Melt Crystallization, *Chemical Engineering Progress*, pp. 52–60, Mar. 1992.

*Primary Examiner*—Gary Geist
(74) *Attorney, Agent, or Firm*—Sheridan Ross P.C.

(57) ABSTRACT

Melt crystallization purification of lactide; and separation and purification of lactides existing in more than one isomeric form.

22 Claims, No Drawings

MELT CRYSTALLIZATION PURIFICATION OF LACTIDES

This is a continuation, of application Ser. No. 08/028,773 filed Feb. 17, 1993, now abandoned.

BACKGROUND OF THE INVENTION

1. Field of the Invention

This invention relates to melt crystallization purification of lactides, including optically active forms thereof, whereby the lactide is substantially completely separated from impurities, including hydroxylic impurities such as water, monomers and oligomeric hydroxycarboxylic acids normally produced along with the lactide during its manufacture, as well as other impurities such as solvents and catalysts. In addition, this invention relates to the separation and purification of lactides existing in more than one isomeric form. Such purification affords the lactides in high and/or controlled states of purity, simply and expeditiously, without the use of selective solvents, fractional crystallization from solvents, distillation or other physical means described in the art.

2. Description of Related Art

Lactide (1,4-dioxane-3,5-dimethyl- 2,5-dione) is an intermediate to high molecular weight polylactic acids disclosed to be useful in biomedical and other applications because of their ability to be degraded biologically and hydrolytically to physiologically and environmentally acceptable by-products.

To achieve the high molecular weights required for such use it is necessary that the lactide be substantially free of hydroxylic (including hydroxycarboxylic) impurities, since such impurities prevent the attainment of desired molecular weights. It is preferred that the acid content of lactide, for example, be less than 10 milliequivalents per kilogram (meq/kg), more preferably less than 5 meq/kg.

Another factor of importance is the stereoisomeric form of the lactide. While lactic acid exists in both a D and L stereoisomeric form, the lactide has in addition a meso form. The racemic mixture of D and L lactides, also of commercial importance, is referred to as the DL lactide. These isomeric lactides have differing stabilities and also give rise to polymers with substantially different properties, making it necessary for some polymer applications to control the ratio of each isomeric form in the final product. These ratios may be controlled either by using processes which make only a single isomer or by purifying a mixture of the isomers. The purification processes in the art are extremely cumbersome and difficult because of the close physical properties of the isomers.

Lactide is most conveniently prepared by polymerizing the corresponding lactic acid to a relatively low molecular weight (oligomeric) polylactic acid, then heating the oligomer, generally in the presence of a catalyst, as is well known in the art, to depolymerize it to the lactide, which is then recovered as a component of a vapor product stream. See Gruter et al, U.S. Pat. No. 1,095,205 (1914); Lowe, U.S. Pat. No. 2,668,162 (1954); Bhatia, U.S. Pat. No. 4,835,293 (1989); DeVries, U.S. Pat. No. 4,797,468 (1989); and Muller, U.S. Pat. No. 5,053,522 (1991), which patents are incorporated herein by reference.

The vapor product stream invariably contains not only the lactide but volatile hydroxylic impurities, among them water, the monomeric lactic acid which is more volatile than the lactide, and often higher boiling oligomers of the lactic acid, all of which are undesirable as they are polymerization chain stoppers which prevent the attainment of desired molecular weights. It may also contain small amounts of solvents or catalysts remaining from previous processing steps. Typically, the vapor product stream contains more than 90% lactides including any isomers and less than 10% impurities.

The typical art procedure for the separation and recovery of the lactide from the vapor product stream generally involves scrubbing with a solvent or crystallization from a solvent. Under such conditions, however, the hydroxylic impurities, particularly water and lactic acid, are capable of undergoing ring-opening reactions with the lactide, resulting in a decrease of lactide yield and an increase of the acidity of the product. The higher the temperature of the recovery process employed, the more likely it is that such reactions will occur.

Moreover, reliance on a solvent, whether for scrubbing the vapor product stream to recover the cyclic ester or for purifying it by recrystallization, is disadvantageous as it necessitates facilities for storing the solvent, using it, purifying it and preventing it from escaping into and contaminating the environment, all of which add significantly to the process investment and operating costs.

An alternate procedure, the purification and recovery of the lactide by distillation and condensation, tends to suffer in that a significant loss of product is often encountered, evidently owing to the reaction of the water and other hydroxylic acid impurities with the lactide at distillation temperatures. Also in the high temperature, acidic environment corrosion of the distillation device can lead to metal ion formation which in turn can catalyze premature lactide polymerization in the equipment itself.

The separation of lactides which are present in more than one isomeric form is even more complex, often involving a combination of multiple solvent recrystallizations and fractional distillations.

Melt crystallization techniques have sometimes been used for purification of certain organic compounds. However, the feasibility of this method cannot be easily predicted. Not only does it depend on the freezing points of the desired product, its impurities and their mixtures with the product, i.e. whether the impurities form a eutectic mixture or a solid solution with the product to be purified, but also on the structure of the crystals formed and therefore their tendency to occlude impurities. Furthermore, the size and productivity of the crystallization equipment depend on the rate at which suitable crystals can be formed without occlusion of the impurities in the crystal structure. As stated in a recent review of this technology (Wynn, "Separate Organics by Melt Crystallization", Chemical Engineering Progress, March 1992, pp 52–60): "Unfortunately, in melt crystallization, the critical steps are rate dependent. They cannot be predicted accurately from theory. Laboratory or pilot-plant data must be generated before even process feasibility can be established."

Further difficulties may arise in cases where the impurities can react with the material to be purified, as is the case with typical impure lactide, making the feasibility of this approach even less predictable.

Thus a need exists for a new and improved solvent-free method of purifying lactides, particularly such lactides contaminated with minor amounts of such hydroxylic impurities as water, monomeric lactic acid and oligomers thereof, which minimizes the disadvantages of prior art methods while simply and expeditiously providing the lactides in high purity suitable for the production of high molecular weight polymers. In addition, a need exists for a solvent-free process for separating isomeric forms of such lactides from its isomers, allowing production of a product with a controlled distribution of isomers.

OBJECTS OF THE INVENTION

It is an object of this invention to provide a process for the purification and recovery of lactide from mixtures containing hydroxylic and/or other impurities without the use of a solvent. It is a further object to provide polymer grade materials having lower concentration of acidic impurities and/or having a controlled isomer composition. It is a still further object to provide a process in which this purification and recovery of polymer grade materials is performed by melt crystallization.

SUMMARY OF THE INVENTION

This invention is a substantially solvent-free process for the purification and recovery of lactides from a non-eutectic mixture comprising a molten or solid lactide and minor proportions of one or more impurities such as hydroxylic impurities or other contaminants by one or more melt crystallization steps. In another embodiment, this invention is a substantially solvent-free process for the purification and recovery of a lactide from a mixture of isomeric forms by one or more melt crystallization steps. Each of the above melt crystallization steps comprises:

cooling a molten lactide mixture to the freezing point of the lactide or slightly below, partially crystallizing the melt and forming a solid phase with lower impurity content and a liquid phase with a higher impurity content, and then separating the solid phase from the liquid phase. Optionally, a still higher purity solid phase can be obtained by a process generally referred to as "sweating": gradually warming the solid phase from the melt crystallization step to a temperature below the melting point of the lactide to selectively melt at least a portion of the remaining impurities together with a minimum amount of the lactide, separating the more purified solid phase and less pure liquid phase, usually recycling the less pure liquid phase to either the melt crystallization or sweating step of the process.

Various types of batch and continuous equipment are known to be useful for melt crystallization and sweating, and may be employed for these steps. Optionally, the above melt purification process may be carried out by zone melting, in which a melted zone is created by heating a narrow zone of a solid lactide, which zone is then moved along the solid material, carrying with it the impurities.

The above general process for melt crystallization can be varied by one skilled in the art to achieve maximum equipment productivity, product purity or yield by carefully adjusting the crystallization and sweating temperatures, and by adjusting the rate of cooling during crystallization and the rate of heating during sweating. Alternatively, the sequence of melting, partially crystallizing to form a liquid and a solid phase, optionally sweating the solid phase, and separating the solid and liquid phases can be repeated until the desired degree of purity is attained. The liquid phase resulting from the initial crystallization step may be subjected to various processes for recovery of valuable materials or to enable partial recycle to the crystallization process to increase yield.

By a substantially solvent-free purification and recovery process is meant the treatment of solid lactide compositions melting between 0° and 200° C. and containing less than about 20% by weight of an inert organic solvent which is non-reactive with the lactide component, or a process in which a small amount of such a solvent is contacted with the above crystalline cake to aid in the removal of occluded liquid. Preferably the lactide composition melts between 40° and 160° C., has a purity including lactides and isomers of greater than 70% by weight and contains less than about 10% by weight of a non-reactive organic solvent, and still more preferably has a lactide purity of greater than 90% and is substantially free of such solvent.

By a non-eutectic lactide composition is meant a composition which does not correspond to a low-melting eutectic composition of the isomeric forms of the lactides which may be present, or of these lactides together with the hydroxylic and other impurities present.

The above lactide compositions are therefore characterized in that the desired purified lactide has a higher melting point than the mixture of lactide with its impurities. For example, the pure L and D lactides each melt at 97° C., while the 50—50 physical mixture of each, the so-called DL lactide, melts at 127° C. In contrast, there are two eutectic compositions at 80-20 and 20-80 ratios of D to L lactide, each of which melt at 94° C. Consequently, to obtain pure L lactide from a mixture with D lactide, the L lactide should be more than 80% and the D lactide less than 20%, or a ratio of L to D of greater than 4 to 1. Similarly, to obtain pure D lactide from a mixture with L lactide, the L lactide should be less than 20% and the D lactide greater than 80%, or an L to D ratio lower than 1 to 4. To obtain the DL lactide from a mixture of D and L lactide, the composition should be between 80% and 20% for each isomer, or an L to D ratio between 4 to 1 and 1 to 4.

The above composition limits may vary somewhat if appreciable amounts of meso isomer are present. In the process of this invention, the meso isomer is removed from the D or L isomers, thereby permitting the meso's recovery in an enriched form. This enriched form is suitable for further purification by methods known in the art, enabling it to be added to lactide compositions for polymers wherein a controlled amount of meso isomer is desired.

The invention is based on the discovery that impure lactides as defined can be separated by melt crystallization from their impurities such as isomeric forms of the lactides and from hydroxycarboxylic acids and other contaminants such as solvents and catalysts, and obtained thereby as polymer grade material. The process of this invention is surprisingly effective and economic, in part because it avoids the expense of using a solvent and in part because it circumvents the tendency of higher temperature purification processes to cause deterioration of the water-lactic acid-lactide system or ionic contamination, premature polymerization of the lactide product.

DESCRIPTION OF THE INVENTION

The invention is applicable to the separation and recovery of lactides from compositions which also include undesirable levels of water, lactic acid and oligomers thereof, as well as such compositions including solvents and catalysts from previous reaction steps. It is particularly applicable to the compositions resulting from the depolymerization of oligomers of the lactic acid and subsequent purification by distillation.

In melting a solid lactide mixture, it is important that this be done at a minimum temperature, to avoid decomposition of the lactide. Preferably this should be no more than 1° to 5° C. above the lactide's melting point. This will vary for each of the stereoisomers and the racemic mixture, and must be determined carefully beforehand.

In cooling the mixture molten to the freezing point of the lactide, this should be accomplished using a cooling medium only slightly below the freezing point of the lactide. Too great a difference in temperature will result in impurities being frozen onto the heat transfer surface simultaneously with the desired pure product, leading to an inadequate purification. The slower rate of cooling must be balanced against the need for multiple melt crystallizations to obtain the desired purity. The optimum conditions are also dependent to some degree on the type of apparatus used for the melt crystallization, and are readily determined for a particular apparatus by one skilled in the art.

The above slow cooling process should continue until the melt is partially crystallized, forming a solid phase with lower impurity content and a liquid phase with a higher impurity content. Crystallizing out too large a fraction of the starting material will result in a product that is too impure for use, and require multiple recrystallizations. Crystallizing out too small a fraction will result in yield losses or the need for recycling too large a fraction of the initial charge. While such variations do not keep the process from being operable, they are not economical of time or equipment usage. The optimum depends of course partly on the purity of the starting material and the desired purity of the product as well as equipment limitations, but again is readily determined for a specific operation by one skilled in the art.

In separating the solid phase from the liquid phase, any convenient method of separating a solid from a liquid may be used. In most cases a simple separation by gravity, i.e. draining, will be adequate. Then the product may be removed from the heat transfer surface by simple melting, again being careful to exceed the melting point by only a few degrees to avoid product decomposition.

A still higher purity solid phase can be obtained by sweating, i.e. gradually warming the solid phase from the melt crystallization step to a temperature below the melting point of the lactide to selectively melt at least a portion of the remaining impurities together with a minimum amount of the lactide. No matter how carefully the initial product is frozen onto the heat transfer surface, a certain amount of the unfrozen melt will adhere to the surface. In addition some material may have been included in the frozen mass as the temperature of the cooling surface was reduced below the lactide's initial freezing point. The sweating process removes both the material adhering to the surface and a portion of the material actually incorporated into the crystal structure. The sweatings removed at this point are ordinarily only slightly below the required product purity, and are conveniently recycled to the next charge of fresh material. In order to avoid large recycle requirements, the sweating process should be operated slowly and carefully, preferably with a method of controlled slow heating using an apparatus such as a time-operated temperature controller equipped for slow and gradual changes in temperature. One such convenient device is a digital temperature controller.

In an optional variation of the above sweating step, a small amount of a washing fluid or solvent may be used to remove the surface-adhering material from the crystallized solid. While this introduces another component to the system, this may not be disadvantageous in systems which already include such a washing fluid or solvent as a pre-existing impurity or in systems which use a washing fluid or solvent in some later steps.

Following the sweating step and the removal of the sweatings by draining or other methods, the purified product may be removed by melting as before.

Various types of batch and continuous equipment may be employed for these steps. A typical static method involves the use of a large tank with multiple heat transfer elements equipped for heating and cooling at a controlled rate or with a controlled temperature differential versus the material in the tank. The product to be purified is simply melted, frozen, drained, sweated, re-drained and the purified product melted as described before. The equipment is easily automated as to require very little attention time or labor requirements.

A typical semi-continuous method involves the use of vertical cooling tubes and a method for pumping the melted crude to the top of the tubes and draining from the bottom. The separate steps are then performed as described before. The process may be made fully continuous by various timing or control devices. A typical apparatus is described in U.S. Pat. No. 3,621,664 and U.S. Pat. No. RE 32,241 (Sulzer), incorporated herein by reference. Numerous other equipment variations are described in subsequent patents by a variety of equipment manufacturers and may also be used for this process.

Optionally, the above purification process may be carried out by zone melting, in which a melted zone is created by heating a narrow zone of a solid lactide mixture, which zone is then moved relative to the solid material, carrying with it the impurities. The critical items to control in this process are the rate of zone movement and the zone temperature. Too slow a zone movement rate will result in low equipment productivity. Too rapid a zone movement will result in inadequate purification. Too high a zone temperature will result in unnecessary product decomposition. A temperature too close to the melting point of the material being processed will result in an inadequate heat transfer rate and therefore low equipment productivity. Optimum conditions and the number of zone purification steps depend on the purity of the material being processed and the required purity of product, but are readily determined by one skilled in the art. Zone melting is more suitable for small scale than large scale processing because of the need for physical separating the solid purified material from the undesired solid residue after the process is complete.

EXAMPLE 1

This example illustrates the use of zone melting for this invention. A glass tube 500 mm long with an internal diameter of 10 mm was partially filled with 50 gms of melted crude lactide while in an upright position and the crude allowed to solidify. A battery of external heaters designed to create melt zones 10 mm in length was set at a temperature of 105° C. The tube was moved through the battery of heaters and an associated cooler at a rate of 30 mm per hour. After 25 passes were made to insure adequate equilibration, the tube was allowed to cool and then broken into 3 pieces along the filled portion to permit analysis of the material at four locations along the tube, here labeled A, B, C and D, with A representing the material at the initially heated end of the tube and D representing material at the tail end of the tube. Isomer distribution was measured by high pressure liquid chromatography, using a commercial Chiral column and internally developed analytical procedures. The acidity was measured by titration with sodium methoxide in a dry solvent medium using phenolphthalein as indicator. The results showed an effective separation of ingredients was taking place for each of the crude samples, as illustrated in the tables below.

TABLE 1

Sample 1 (670 Meq/kg crude L Lactide)

| Analysis | Initial | Zone A | Zone B | Zone C | Zone D |
|---|---|---|---|---|---|
| Acidity, meq/kg | 670 | 25 | 150 | 950 | 1400 |
| Total lactide | 89.2% | 99.6% | 97.6% | 84.6% | 77.3% |
| Isomer distribution: | | | | | |
| L lactide | 93.0% | 100.0% | 97.5% | 75.1% | 63.2% |
| D lactide | 1.0% | 0.0% | 0.0% | 5.1% | 5.0% |
| Meso lactide | 6.0% | 0.0% | 2.6% | 19.8% | 31.7% |

Note 1: In Table 1 and following tables, the total lactide % was estimated by assuming that the only non-lactide impurities are the acidic ingredients measured above and that their average molecular weight is 162 (corresponding to the linear dimer of lactic acid).

Not only was the acidity lowered from 670 to 25 meq/kg in Zone A, and the corresponding total lactide purity improved from 89.2% to 99.6%, but the D lactide and meso lactide isomers were also completely removed from the L lactide.

In addition, the meso lactide concentration in the last zone was increased five-fold over the initial value. This greatly increases the ease of refining the meso further by methods known in the art. Furthermore, after its acidic impurities are removed, this high-meso material may be blended into to a lactide mixture prior to polymerization to achieve a controlled meso concentration, desirable for certain applications.

TABLE 2

Sample 2 (450 Meq/kg crude L Lactide)

| Analysis | Initial | Zone A | Zone B | Zone C | Zone D |
|---|---|---|---|---|---|
| Acidity, meq/kg | 450 | 8 | 240 | 1000 | 2300 |
| Total lactide | 92.7% | 99.87% | 96.1% | 83.8% | 62.7% |
| Isomer distribution: | | | | | |
| L lactide | 95.5% | 100.0% | 97.0% | 87.9% | 81.6% |
| D lactide | 0.5% | 0.0% | 0.0% | 1.9% | 2.8% |
| Meso lactide | 4.0% | 0.0% | 3.0% | 10.2% | 15.6% |

In this case, by starting with a slightly purer lactide sample, an even higher purity was obtained in Zone A. The meso lactide concentration in the last zone was increased nearly four-fold.

TABLE 3

Sample 3 (20 Meq/kg crude L Lactide)

| Analysis | Initial | Zone A | Zone B | Zone C | Zone D |
|---|---|---|---|---|---|
| Acidity, meq/kg | 20 | 1.8 | 2.5 | 3.4 | 147 |
| Total lactide | 99.7% | 99.97% | 99.96% | 99.94% | 97.6% |
| Isomer distribution: | | | | | |
| L lactide | 98.0% | 100.0% | 100.0% | 100.0% | 86.1% |
| D lactide | 0.0% | 0.0% | 0.0% | 0.0% | 0.0% |
| Meso lactide | 2.0% | 0.0% | 0.0% | 0.0% | 13.9% |

In this case, the acidity in the material in Zone A was reduced to a very low 1.8 Meq/kg, and the meso concentration was enriched nearly seven-fold.

EXAMPLE 2

A sample of DL crude lactide containing approximately 53% L lactide, 40% D lactide and 7% meso lactide had an acidity of 597 meq/kg. This sample was then cold-water washed as follows: The sample was mixed with four times its weight of 0° C. water for 2 to 3 seconds and then promptly filtered. The wet cake was then dried in a vacuum aspirator at 0% relative humidity, 25° C. and 80 mm Hg pressure for 1 to 4 hours or until dry. The acidity was thereby reduced to about 150 meq/kg with little effect on isomer ratio.

The zone melting procedure of Example 1 was then repeated o n the cold-water washed sample of crude DL lactide. In this case the product of the zone refining was divided into 5 zones.

TABLE 4

Sample 4 (150 Meq/kg crude DL Lactide)

| Analysis | Initial | Zone A | Zone B | Zone C | Zone D | Zone E |
|---|---|---|---|---|---|---|
| Acidity, meq/kg | 150 | 1.9 | 2.0 | 38.2 | 357 | 462 |
| Total lact. | 99.57% | 99.97% | 99.97% | 99.38% | 94.22% | 92.25% |
| Isomer distribution: | | | | | | |
| L lactide | 53.2% | 49.9% | 49.8% | 50.1% | 55.4% | 57.7% |
| D lactide | 39.8% | 50.1% | 50.2% | 49.4% | 32.8% | 27.1% |
| Meso lact. | 6.9% | 0.0% | 0.0% | 0.5% | 11.7% | 15.2% |

In this case, the acidity in the material in Zone A was reduced to 1.9 meq/kg, similar to the results on the crude L lactide above. Remarkably, the isomer distribution in the material in Zones A, B and C was brought to exactly the theoretical 50—50 racemic composition of DL lactide within analytical accuracy, the excess L lactide being moved to Zones D and E. Furthermore, the meso isomer was entirely removed from the material in Zones A and B. The meso content in Zone E was enriched to more than double the amount in the original sample.

EXAMPLE 3

This example illustrates the use of a falling film crystallizer for this invention. A vertical crystallization tube, 12 meters long with 70 mm internal diameter, was equipped with an external jacket for controlled cooling, a 35 liter sump tank to collect liquid draining from the tube, and a recycle pump. Then 33.5 Kg of lactide crude was melted in the sump tank using a heating temperature of 110° C., and then sampled for analysis. The molten crude was pumped to the top of the crystallization tube and the material leaving the bottom was collected in the sump tank and recycled back to the top of the tube. To initiate crystallization, the outer shell heat transfer fluid on the tube was cooled to a 90° C. mean temperature in 5 minutes. The tube was then cooled at a rate of 0.5° C. per minute. As the tube was progressively chilled, material began to freeze on the wall of the crystallizer tube and the level of liquid in the sump tank began to drop. The temperature of the tube wall was progressively lowered throughout the freezing process to maintain a reasonable freezing rate and overcome the insulating effect of increasing organic solid thickness and the progressive freezing point reduction with increased impurity levels in the material being frozen. Once the level of liquid in the sump tank dropped to a chosen level, the liquid "residue" in it was drained and analyzed. Typically this was done when the liquid in the sump tank was ¼ to ⅕ of the initial feed mass. With the residue removed from the system, the crystallizer tube surface was quickly warmed close to the melting point of the pure material (from 55° C. to 95° C. in 10 minutes), and then slowly and carefully warmed at a rate of 0.15° C. per minute. Successive "sweating" fractions were collected during this process. The total sweating fraction was usually about 5% to 10% of the initial feed. The sweating fraction was then removed from the system for analysis and possible later recycle. The crystallizer tube was then heated at a rate of 2° C. per minute starting with 97° C., until the material frozen on the crystallizer tube was melted and collected in the sump tank. This material was then sent back through the crystallizer tube for a second stage purification using the same procedure as before. Second stage residue and sweating fractions were again collected and segregated. The second stage product weighed 17.6 Kg and was found to have less than 1 meq/Kg acidity compared to an initial value of 52 meq/Kg.

In a typical crystallization run, about 70 minutes was spent in the initial freezing step, about 10 minutes in carefully returning the tube to the melting point, about 15 minutes in the sweating stage and about 5 minutes in the final product melting. Typical flow rates based on the above tube size were in the range of 10 to 20 kg per minute.

TABLE 5

(First Crystallization)

| Analysis | Initial | Product | Sweatings | Residue |
|---|---|---|---|---|
| Acidity, meq/kg | 52 | 2.7 | 137 | 204 |
| Total lactide | 99.2% | 99.96% | 97.8% | 96.7% |
| Isomer distribution: | | | | |
| L lactide | 99.0% | 100.0% | 98.4% | 97.2% |
| D lactide | 0.0% | 0.0% | 0.0% | 0.0% |
| Meso lactide | 1.0% | 0.0% | 1.6% | 2.8% |

This example illustrates that similar results to zone purification are obtainable in equipment suitable for large-scale processing.

TABLE 6

(Second Crystallization)

| Analysis | Initial | Product | Sweatings + Residue |
|---|---|---|---|
| Acidity, meq/kg | 2.7 | 0.7 | 7.7 |
| Total lactide | 99.96% | 99.99% | 99.88% |
| Isomer distribution: | | | |
| L lactide | 100.0% | 100.0% | 100.0% |
| D lactide | 0.0% | 0.0% | 0.0% |
| Meso lactide | 0.0% | 0.0% | 0.0% |

This illustrates that a still higher purity product may be obtained by a second melt crystallization step.

EXAMPLE 4

The second stage crystallization residue and sweating fractions from Example 3 were then combined with additional crude feed to make up a new crystallization charge. This was again given two crystallization treatments as in Example 3. The second stage product weighed 15.3 Kg compared to an initial weight of 33.3 Kg, and was found to have less than 1 meq/Kg acidity compared to an initial value of 42 meq/Kg, essentially duplicating the improvement shown in Example 3.

Table 7

(First Crystallization)

| Analysis | Initial | Product | Sweatings | Residue |
|---|---|---|---|---|
| Acidity, meq/kg | 42 | 2.8 | 29.5 | 167 |
| Total lactide | 99.3% | 99.95% | 99.52% | 97.3% |
| Isomer distribution: | | | | |
| L lactide | 99.0% | 100.0% | 100.0% | 97.6% |
| D lactide | 0.0% | 0.0% | 0.0% | 0.0% |
| Meso lactide | 1.0% | 0.0% | 0.0% | 2.4% |

TABLE 8

(Second Crystallization)

| Analysis | Initial | Product | Sweatings | Residue |
|---|---|---|---|---|
| Acidity, meq/kg | 2.8 | 0.8 | 2.0 | 5.8 |
| Total lactide | 99.95% | 99.99% | 99.97% | 99.91% |
| Isomer distribution: | | | | |
| L lactide | 100.0% | 100.0% | 100.0% | 100.0% |
| D lactide | 0.0% | 0.0% | 0.0% | 0.0% |
| Meso lactide | 0.0% | 0.0% | 0.0% | 0.0% |

EXAMPLE 5

A number of residues and sweating fractions from various experiments were combined to give a feed stock with 163 meq/Kg acidity, more than 3 times the acidity in Examples 3 and 4. This material was twice crystallized as in Example 3. The second stage product weighed 15.4 Kg compared to an initial weight of 31.7 Kg, and was found to have approximately 1 meq/Kg acidity. The first stage residue showed more than a 5-fold enrichment of the meso content.

TABLE 9

(First Crystallization)

| Analysis | Initial | Product | Sweatings | Residue |
|---|---|---|---|---|
| Acidity, meq/kg | 163 | 12.9 | 349 | 694 |
| Total lactide | 97.4% | 99.79% | 94.4% | 88.8% |
| Isomer distribution: | | | | |
| L lactide | 98.0% | 100.0% | 95.1% | 89.9% |
| D lactide | 0.0% | 0.0% | 0.0% | 0.0% |
| Meso lactide | 2.0% | 0.0% | 4.9% | 11.1% |

TABLE 10

(Second Crystallization)

| Analysis | Initial | Product | Sweatings | Residue |
|---|---|---|---|---|
| Acidity, meq/kg | 12.9 | 1.1 | 11 | 42 |
| Total lactide | 99.79.% | 99.98% | 99.82% | 99.32% |
| Isomer distribution: | | | | |
| L lactide | 100.0% | 100.0% | 100.0% | 98.7% |
| D lactide | 0.0% | 0.0% | 0.0% | 0.0% |
| Meso lactide | 0.0% | 0.0% | 0.0% | 1.3% |

EXAMPLE 6

Samples of products from Examples 3 to 5 were given a standardized polymerization test to measure the effect of reducing the acidity on the rate of polymerization. A faster rate is desirable because it leads to higher productivity in the polymerization equipment. The polymerization was carried out at a temperature of 188° C. The number of minutes required to reach 85% conversion was used for comparing results between samples. Results are summarized in the table below:

TABLE 11

Standard Polymerization Tests

| No. of Samples Time Tested | Acidity Level Meq/kg | 85% Conversion Minutes (average) |
|---|---|---|
| 4 | <2.1 | 3 |
| 8 | 2.1 to 4.0 | 6 |
| 3 | 4.0 to 12.0 | 10 |

The above results clearly show the benefit of the low acidity levels achievable with our invention.

EXAMPLE 7

A sample of L lactide weighing 25.7 Kg was fed to the falling film crystallizer described in Example 3 and circulated at 115° C. for 0.5 hours. A sample was taken and found to have an acidity of 200 meq/Kg acidity. This material was then crystallized as in Example 3, except that only a single crystallization was used. However, the sweatings were isolated in two portions and analyzed separately. The final product weighed 17.3 Kg and was found to have approximately 18 meq/Kg acidity. The samples were also analyzed for metals content to determine the metals purification effect of this melt crystallization. The tin content was the result of residual catalyst from previous steps; the iron, chromium and nickel are the result of some equipment corrosion in previous steps. The results are summarized in the table below.

TABLE 12

(Single Crystallization)

| Analysis | Initial Residue | Product | Sweating First | Cuts | Second |
|---|---|---|---|---|---|
| Acidity, meq/kg | 200 | 18.0 | 644 | 175 | 608 |
| Total lactide | 96.7% | 99.71% | 89.6% | 97.2% | 90.2% |
| Isomer distribution: | | | | | |
| L lactide | 97.5% | 99.8% | 93.1% | 98.6% | 92.5% |
| D lactide | 0.8% | 0.0% | 1.3% | 0.3% | 1.6% |
| Meso lactide | 1.8% | 0.2% | 5.6% | 1.1% | 6.0% |
| Metals analyses: | | | | | |
| Tin, ppm | 5 | 1 | 20 | 10 | 20 |
| Iron, ppm | 2 | <1 | 20 | 3 | 20 |
| Chromium, ppm | <1 | <1 | 1 | <1 | 3 |
| Nickel, ppm | <1 | <1 | 2 | <1 | 2 |

As shown by these results, not only are the acidic impurities and isomeric impurities largely removed by a single melt crystallization step, but the metallic impurities are nearly all removed as well. In samples of lactide which contained methyl isobutyl ketone solvent, most of the solvent was also similarly removed, as shown clearly by odor comparisons.

We claim:

1. A solvent-free method for the purification of a non-eutectic lactide mixture derived from the depolymerizaton of lactic acid oligomers comprising by weight a major amount of one lactide isomer and a minor amount of at least one other lactide isomer and acidic and other impurities comprising the steps:
    (1) melting the lactide mixture;
    (2) cooling the molten lactide mixture to the freeze point or slightly below the freeze point of the lactide mixture to effect partial crystallization of the mixture and formation of a solid phase having a higher content than the molten mixture of the major isomer and a lower content of the minor isomer(s) and acidic and other impurities;
    (3) separating the solid phase from the liquid phase;
    (4) forming an additional molten mixture by melting the separated solid phase; and
    (5) repeating steps (2)–(4) with the additional molten mixture until a predetermined degree of putity is obtained in the separated solid phase.

2. A solvent-free method for the purification of a lactide mixture derived from the depolymerization of lactic acid oligomers comprising by weight a major amount of one lactide isomer and a minor amount of at least one other lactide isomer and acidic and other impurities comprising the steps:
    (1) melting the lactide mixture;
    (2) cooling the molten lactide mixture to the freeze point or slightly below the freeze point of the lactide mixture to effect partial crystallization of the mixture and formation of a solid phase having a higher contenty than the molten mixture of the major isomer and a lower content of the minor isomer(s) and acidic and other impurities;
    (3) separating the solid phase from the liquid phase;
    (4) forming a further liquid phase by gradually warming the separated solid phase to a temperature below its melting point;
    (5) separating the solid phase form the further liquid phase; and
    (6) repeating steps (2)–(4) until a predetermined degree of purity is obtained in the separated solid phase.

3. The method of claims 1 or 2 in which the lactide mixture is comprised of more than 80% by weight of the major isomer.

4. The method of claim 3 in which the major isomer is L lactide.

5. The method of claim 3 in which the major isomer is D lactide.

6. A solvent-free method for the recover of DL lactide from a non-eutectic lactide mixture derived from the depolymerization of lactic acid oligomers comprising between 20 and 80% by weight each of D and L lactide and a minor amount of acidic and other impurities comprising the steps:
    (1) melting the lactide mixture;
    (2) cooling the molten lactide mixture to the freeze point or slightly below the freeze point of the lactide mixture to effect partial crystallization of the mixture and formation of a solid phase comprising DL lactide and a lowe content of acidity and other impurities;
    (3) separating the solid phase from the liquid phase;
    (4) forming an additional molten mixture by melting the separated solid phase; and
    (5) repeating steps (2)–(4) with the addtional molten mixture until a predetermined degree of purity is obtained in the separated solid phase.

7. The method of claims 1, 2 or 6 in which the acidity of the separated solid phase is reduced to below 10 meq/kg.

8. The method of claim 1 or 2 carried out in a falling film crystallizer.

9. The method of claim 2 or 6 carried out in a static crystallizer.

10. The method of claim 1 carried out in a zone melt purifier.

11. A process for the melt recrystallization of lactide, comprising (a) heating lactide to a temperature suffiecent to form a melt;

(b) cooling the melt in at least one recrystallizer to cause a lactide composition having a relatively higher content of a major isomer to crystallize on a surface of the recrystallizer while maintaining a lactide composition having a relatively lower content of the major isomer and a relatively higher content of impurities in a liquid phase; and (c) separating the crystallized lactide composition from the liquid lactide composition.

12. The process of claim 11, wherein the lactide in step (a) comprises a non-eutectic lactide mixture derived from the depolymerization of lactic acid oligomers comprising by weight a major amount of at least one lactide isomer and a minor amount of at least one other lactide isomer and acidic and other impurities.

13. The process of claim 11, wherein said process comprises a solvent-free process.

14. The process of claim 11, wherein steps (a) through (c) are repeated on the crystallized lactide composition obtained in step (c) until a crystallized lactide composition having a predetermined content of the major isomer is obtained.

15. The process of claim 11, further comprising the steps of (d) gradually warming the crystallized lactide composition to a temperature below its melting point to form a liquid phase; and (e) separating the liquid phase from the crystallized lactide composition.

16. The process of claim 15, wherein the lactide in step (a) comprises a non-eutectic lactide mixture derived from the depolymerization of lactic acid oligomers comprising by weight a major amount of at least one lactide isomer and a minor amount of at least one other lactide isomer and acidic and other impurities.

17. The process of claim 16, wherein steps (a) through (e) are repeated on the crystallized lactide composition obtained in step (e) until a crystallized lactide composition having a predetermine copntent of the major isomer is obtained.

18. The process of claim 15, wherein steps (a) through (e) are repeated on the crystallzed lactide composition obtained in step (e) until a crystallized lactide composition having a predetermined content of a major isomer is obtained.

19. The process of claim 11, wherein the step (a) comprises heating lactide to a temperature of 110° C. and wherein step (b) comprises cooling the melt to a temperature of 90° C.

20. The method of claim 5 carried out in a falling film crystallizer.

21. The method of claim 5 carried out in a static crystallizer.

22. The method of claim 5 carried out in a zone melt purifier.

* * * * *